(12) United States Patent
Shue et al.

(10) Patent No.: US 7,044,935 B2
(45) Date of Patent: May 16, 2006

(54) INTRAVENOUS CATHETER INTRODUCING DEVICE

(76) Inventors: Ming-Jeng Shue, No. 14, Lane 8, Chung-I St., Hsi Dist., Taichung City (TW); Phillip Shue, No. 14, Lane 8, Chung-I St., Hsi Dist., Taichung City (TW); Deborah Huang, 7F, No. 5, Sec. 3, Liu-Chun E. St., Chung Dist., Taichung City (TW)

( * ) Notice: Subject to any disclaimer, the term of this patent is extended or adjusted under 35 U.S.C. 154(b) by 54 days.

(21) Appl. No.: 10/826,543

(22) Filed: Apr. 15, 2004

(65) Prior Publication Data
US 2005/0101914 A1    May 12, 2005

(30) Foreign Application Priority Data
Nov. 7, 2003    (TW) .............................. 92131220 A

(51) Int. Cl.
*A61M 5/178* (2006.01)
(52) U.S. Cl. ................................................ 604/164.01
(58) Field of Classification Search ........... 604/164.01, 604/164.06, 164.07, 164.12, 165.01, 165.02, 604/168.01; 128/919
See application file for complete search history.

(56) References Cited

U.S. PATENT DOCUMENTS

| | | | | |
|---|---|---|---|---|
| 5,321,359 A | * | 6/1994 | Schneider | .................... 324/307 |
| 5,575,773 A | | 11/1996 | Song et al. | |
| 5,951,515 A | * | 9/1999 | Osterlind | ..................... 604/110 |
| 6,077,244 A | * | 6/2000 | Botich et al. | ................ 604/110 |
| 6,193,690 B1 | * | 2/2001 | Dysarz | ....................... 604/161 |
| 6,325,781 B1 | | 12/2001 | Takagi et al. | |
| 6,547,762 B1 | * | 4/2003 | Botich et al. | ............... 604/110 |
| 6,663,592 B1 | * | 12/2003 | Rhad et al. | ................. 604/110 |

FOREIGN PATENT DOCUMENTS

| | | |
|---|---|---|
| WO | WO 97/05912 A2 | 2/1997 |
| WO | WO 02/41932 A2 | 5/2002 |

* cited by examiner

*Primary Examiner*—LoAn H. Thanh
(74) *Attorney, Agent, or Firm*—Townsend and Townsend and Crew LLP

(57) ABSTRACT

An intravenous catheter introducing device includes a needle hub inserted into and axially slidable relative to an inner barrel wall surface of a barrel. The needle hub holds a needle cannula and permits the cannula to extend forwardly of the barrel for ready use. A catheter connection assembly is detachably sleeved on a front smaller-diameter wall portion of the barrel and permits a tip end of the needle cannula to project forwardly of a tubular cannula of the assembly. A releasably retaining member includes a retaining hole formed in a rear larger-diameter wall portion of the barrel, and a radially extending engaging peg engageable in the hole. Operation of an actuator mounted on the peg can disengage the peg from the hole so as to permit axial movement of the needle hub for drawing the needle cannula within the barrel.

11 Claims, 13 Drawing Sheets

INTRAVENOUS CATHETER INTRODUCING DEVICE

BACKGROUND OF THE INVENTION

1. Field of the Invention

This invention relates to an intravenous catheter introducing device, more particularly to an intravenous catheter introducing device with a needle cannula which is retractable into a barrel for safe disposal.

2. Description of the Related Art

Referring to FIGS. 1 and 2, a self-retracting IV catheter introducer disclosed in U.S. Pat. No. 5,989,220 is shown to include a catheter connector assembly including a barrel 10 enclosing a retraction body 11 which has a front portion 111 that carries a needle cannula 12 and that extends through an opening in front of the barrel 10, and a rear portion 112 that is mounted within the barrel 10. The front portion 111 has a connection surface 111a which is frictionally engaged with a corresponding connection surface 131 of a catheter hub 13 so as to prevent rearward retraction of the retraction body 11. A biasing spring 15 is compressed against a ledge 101 at the front of the barrel 10, and a spring seat 113 of the retraction body 11. In use, the needle cannula 12 which extends through a flexible catheter 14 is inserted into a patient's vein to introduce the catheter 14 into the vein for intravenous delivery of fluid. The catheter hub 13 is then separated from the retraction body 11 by forcibly pulling the barrel 10 while holding the catheter hub 13 so that the catheter hub 13 is separated from the front portion 111 of the retraction body 11 by loosening of the connection surface 111a, and the retraction body 11 is immediately and automatically forced into the barrel 10 by the biasing spring 15, thereby drawing the used needle cannula 12 behind it. However, since the needle cannula 12 is drawn as soon as the catheter hub 13 is disengaged from the retraction body 11, the drawing operation is not manually controllable, which may lead to an undesirable withdrawal of the needle cannula 12 that may result in an accident, such as dropping of the barrel 10.

SUMMARY OF THE INVENTION

An object of the present invention is to provide an intravenous catheter introducing device which can be operated easily and safely to retract a used needle cannula with one hand.

According to this invention, the intravenous catheter introducing device includes a barrel, a needle cannula, a needle hub, a releasably retaining member, an actuator, and a catheter connection assembly.

The barrel has front and rear open ends opposite to each other in a longitudinal direction, and a surrounding barrel wall interconnecting and interposed between the front and rear open ends. The surrounding barrel wall includes a front smaller-diameter wall portion and a rear larger-diameter wall portion which are opposite to each other in the longitudinal direction and which are proximate to the front and rear open ends, respectively. The surrounding barrel wall has an inner barrel wall surface which surrounds an axis in the longitudinal direction and which confines a passage that is communicated with the front and rear open ends, and an outer barrel wall surface opposite to the inner barrel wall surface in radial directions relative to the axis.

The needle cannula has a front segment terminating at a tip end, and a rear connecting end opposite to the front segment along the axis.

The needle hub includes a front holding portion and a rear shell portion disposed opposite to each other along the axis. The rear shell portion is inserted into the passage from the rear open end, and is slidable relative to the surrounding barrel wall along the axis between front and rear positions to be proximate to the front open end and the rear open end, respectively. The front holding portion holds the rear connecting end of the needle cannula such that when the rear shell portion is in the front position, the needle cannula is placed in a position of use, where the front segment extends forwardly of the front open end for ready use, and when the rear shell portion is in the rear position, the needle cannula is placed in a disposal position, where the front segment retreats into the passage. The rear shell portion surrounds the axis and defines a flashback chamber fluidly communicated with the needle cannula.

The releasably retaining member is disposed to arrest axial movement of the needle hub relative to the barrel when the rear shell portion of the needle hub is in the front position, and includes a retaining hole and an engaging peg. The retaining hole is formed in the outer barrel wall surface of the larger-diameter wall portion, and extends in a radial direction through the inner barrel wall surface. The engaging peg is disposed to extend in the radial direction, and is engageable in the retaining hole to establish an interengagement between the larger-diameter wall portion and the rear shell portion such that movement of the rear shell portion of the needle hub at the front position is arrested.

The actuator is operable externally and is disposed to enable the engaging peg to be disengaged from the retaining hole so as to permit the axial movement of the needle hub to the rear position.

The catheter connection assembly includes a catheter hub and a tubular catheter. The catheter hub includes a sleeve portion which is detachably sleeved relative to the front holding portion of the needle hub and which defines a duct along the axis, and a tip portion which is opposite to the sleeve portion along the axis, and which defines a through hole that is communicated with the duct along the axis and that permits extension of the front segment therethrough. The tubular catheter has a proximate segment which is inserted into the through hole and which extends along the axis to be fluidly communicated with the duct, and a distal segment which extends from the proximate segment along the axis to extend forwardly of the tip portion so as to surround and sheathe the front segment of the needle cannula while permitting the tip end to project forwardly of the distal segment when the needle cannula is placed in the position of use.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
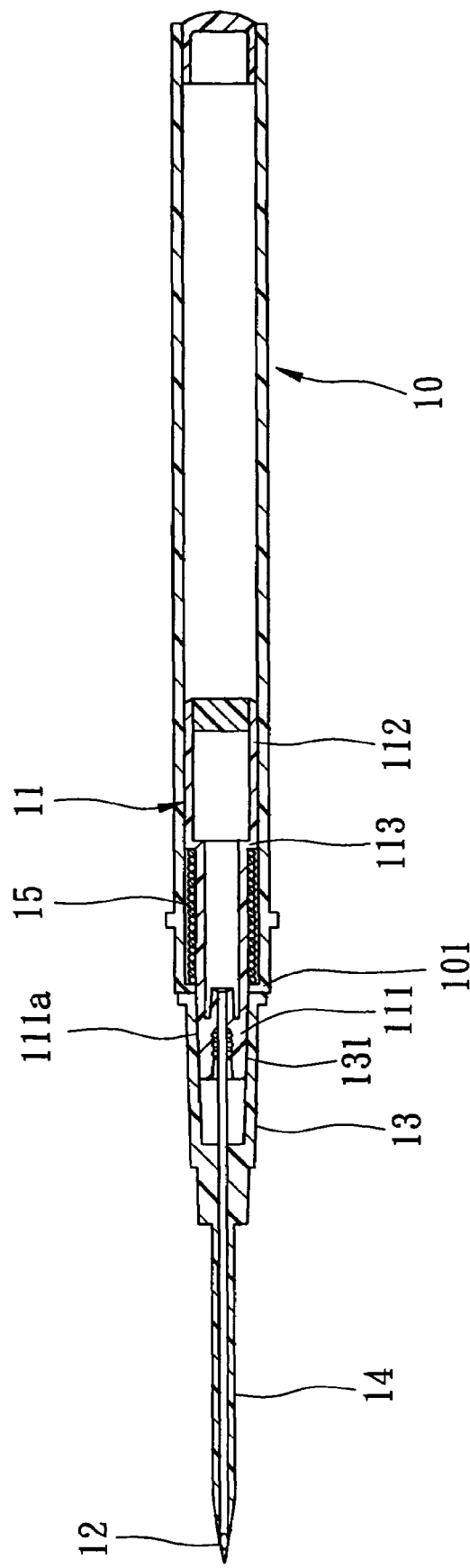
FIG. 1 is a sectional view of a conventional IV catheter introducer in a ready-to-use position.
Figure 2:
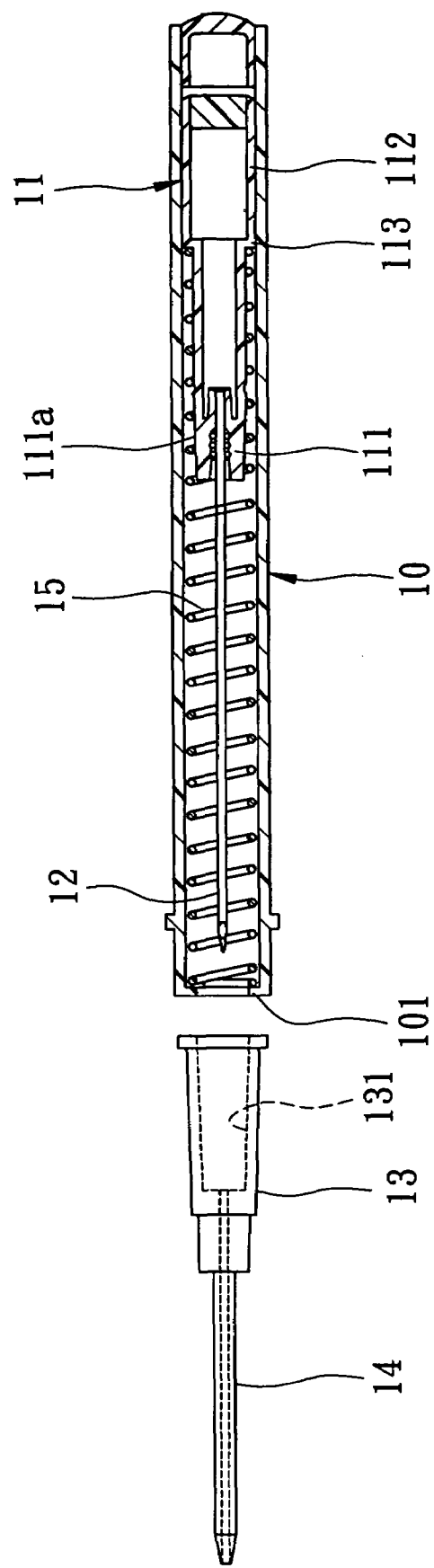
FIG. 2 is a sectional view of the conventional IV catheter introducer in a retracted position.

Before the present invention is described in greater detail, it should be noted that same reference numerals have been used to denote like elements throughout the specification.

Figure 3:
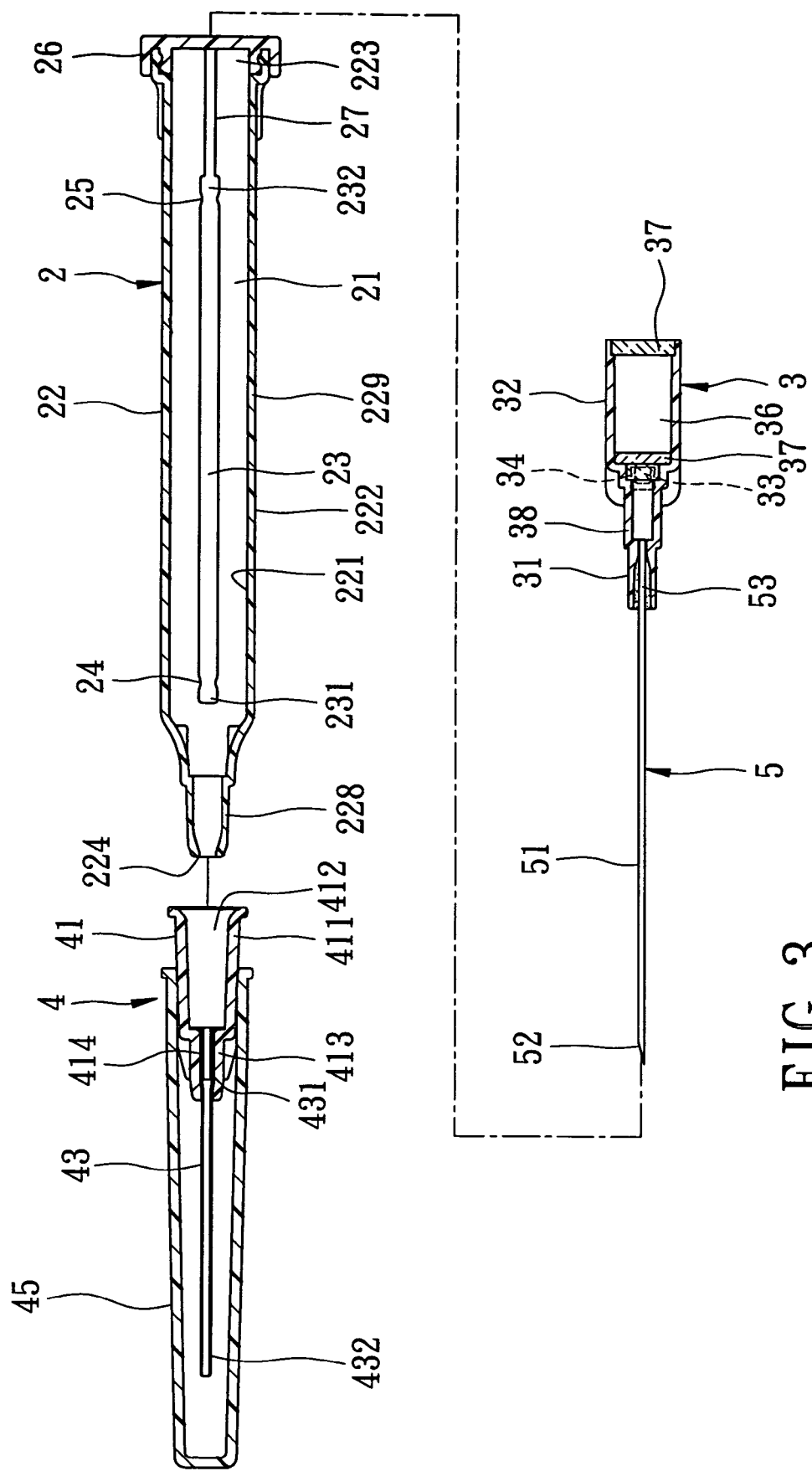
FIG. 3 is an exploded sectional view of a first preferred embodiment of an intravenous catheter introducing device according to this invention.
Figure 4:
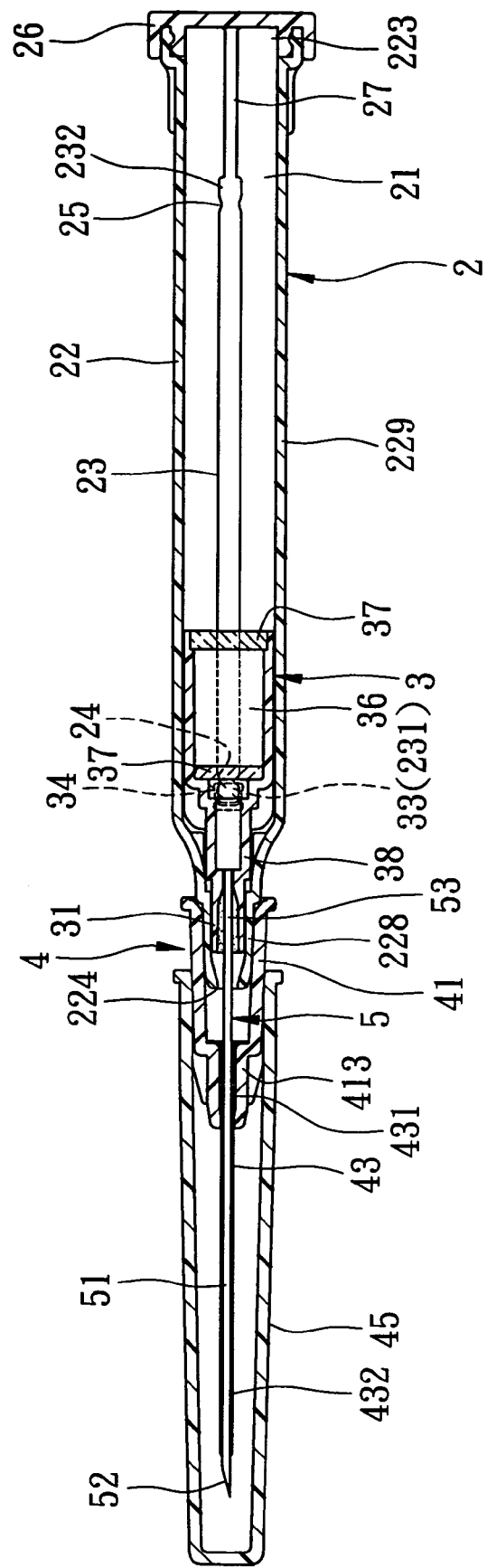
FIG. 4 is a sectional view of the first preferred embodiment in a ready-to-use position.

Referring to FIGS. 3 and 4, the preferred embodiment of an intravenous catheter introducing device according to the present invention is shown to comprise a barrel 2, a needle hub 3, a needle cannula 5, and a catheter connection assembly 4.

The barrel 2 has front and rear open ends 224,223 opposite to each other in a longitudinal direction, and a surrounding barrel wall 22 which interconnects and which is interposed between the front and rear open ends 224,223. The surrounding barrel wall 22 includes a front smaller-diameter wall portion 228 and a rear larger-diameter wall portion 229 which are opposite to each other in the longitudinal direction and which are proximate to the front and rear open ends 224,223, respectively. The surrounding barrel wall 22 has an inner barrel wall surface 221 which surrounds an axis in the longitudinal direction and which confines a passage 21 communicated with the front and rear open ends 224,223, and an outer barrel wall surface 222 opposite to the inner barrel wall surface 221 in radial directions relative to the axis.

A releasably retaining member includes a retaining hole 231 which is formed in the outer barrel wall surface 222 of the larger-diameter wall portion 229, and which extends in a radial direction through the inner barrel wall surface 221. The rear larger-diameter wall portion 229 has an elongated guideway 23 which extends from the outer barrel wall surface 222 through the inner barrel wall surface 221 in the radial direction, and which is elongated from the retaining hole 231 rearwardly and in the longitudinal direction to terminate at a rear retaining end 232. The elongated guideway 23 has front and rear constricted regions 24,25 which are formed immediately behind the retaining hole 231 and immediately in front of the rear retaining end 232, respectively.

Figure 5:
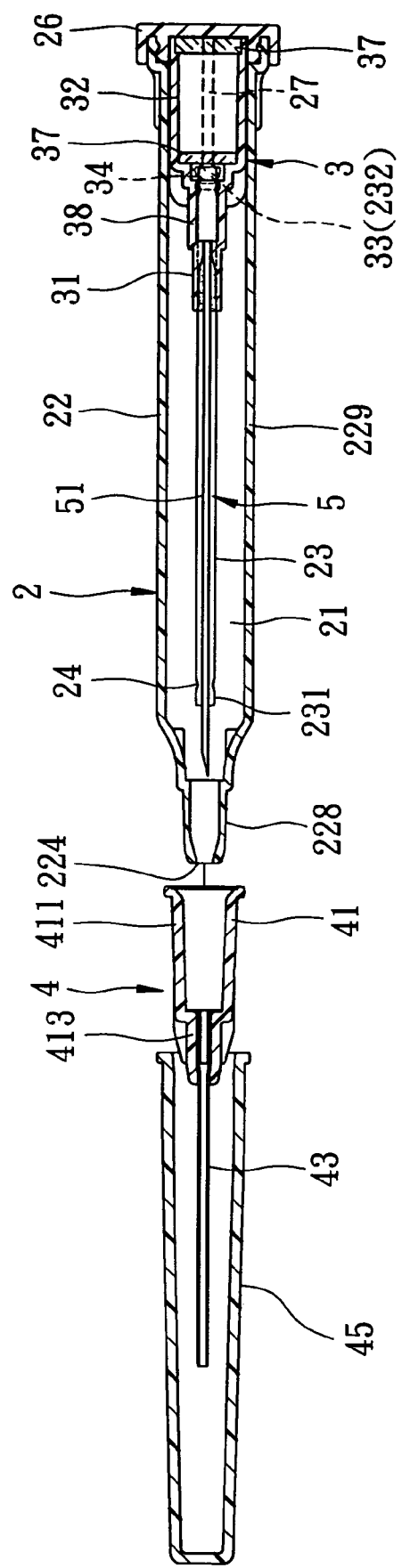
FIG. 5 is a sectional view of the first preferred embodiment in a retracted position.

The needle cannula 5 has a front segment 51 terminating at a tip end 52, and a rear connecting end 53 opposite to the front segment 51 along the axis. The needle hub 3 is inserted into the passage 21 from the rear open end 223, which is closed by a closure cap 26, and is slidable relative to the surrounding barrel wall 22 along the axis between front and rear positions to be proximate to the front open end 224 and the rear open end 223, respectively. The needle hub 3 includes a front holding portion 31 which holds the rear connecting end 53 of the needle cannula 5 such that when the needle hub 3 is in the front position, the needle cannula 5 is placed in a position of use, as shown in FIG. 4, where the front segment 51 extends forwardly of the front open end 224 for ready use, and when the needle hub 3 is in the rear position, the needle cannula 5 is placed in a disposal position, as shown in FIG. 5, where the front segment 51 retreats into the passage 21. The needle hub 3 further includes a rear shell portion 32 which is disposed opposite to the front holding portion 31 along the axis and which is received in the passage 21 at the larger-diameter wall portion 229. The rear shell portion 32 surrounds the axis and defines a flashback chamber 36 which is fluidly communicated with the needle cannula 5. Two air-permeable members 37 are in engagement with the rear shell portion 32 to enclose the flashback chamber 36, and are made from a porous filter material for passage of air displaced by the fluid so as to restrain the possible fast flashback blood flow. In addition, the needle hub 3 has an intermediate portion 38 which interconnects the front holding portion 31 and the rear shell portion 32 to communicate the needle cannula 5 with the flashback chamber 36 and which is light transmissible to permit viewing of blood flowing therethrough.

The releasably retaining member further includes an engaging peg 33 disposed on and extending in the radial direction from the rear shell portion 32 to terminate at a shifted end which extends radially and outwardly of the outer barrel wall surface 222. The engaging peg 33 is slidable along the elongated guideway 23 from the retaining hole 231 to the rear retaining end 232 when the needle hub 3 slides from the front position to the rear position. Thus, the engaging peg 33 is engageable in the retaining hole 231 or the rear retaining end 232 to form an interengagement between the larger-diameter wall portion 229 and the rear shell portion 32. When the needle hub 3 is disposed at the front or rear position, axial movement of the needle hub 3 relative to the barrel 2 is arrested by a corresponding one of the front and rear constricted regions 24,25. Once the engaging peg 33 is forced through one of the front and rear constricted regions 24,25, movement of the engaging peg 33 is arrested by virtue of a snap-fit in a corresponding one of the retaining hole 231 and the rear retaining end 232 so as to position the needle hub 3 in a corresponding one of the front and rear positions. The larger-diameter wall portion 229 further has a split 27 which extends from the rear retaining end 232 to the rear open end 223 so as to vest the elongated guideway 23 with an increased flexibility along the radial direction, thereby facilitating the forced movement of the engaging peg 33 through the front and rear constricted regions 24,25, and facilitating the insertion of the engaging peg 33 into the elongate guideway 23 through the split 27.

An enlarged actuator 34 is formed integrally with the shifted end of the engaging peg 33, and is disposed outwardly of and is slidable relative to the outer barrel wall surface 222 so as to be disengaged from the retaining hole 231, thereby permitting the axial movement of the needle hub 3 to the rear position along the elongated guideway 23.

The catheter connection assembly 4 includes a catheter hub 41, a flexible tubular catheter 43, and a tip protector 45.

The catheter hub 41 includes a sleeve portion 411 which is detachably sleeved on the smaller-diameter wall portion 228 of the barrel 2 and which defines a duct 412 along the axis, and a tip portion 413 which is opposite to the sleeve portion 411 along the axis, and which defines a through hole 414 that communicates with the duct 412 along the axis, and that permits extension of the front segment 51 of the needle cannula 5 therethrough.

The tubular catheter 43 has a proximate segment 431 which is inserted into the through hole 414 and which extends along the axis to be fluidly communicated with the duct 412, and a distal segment 432 which extends from the proximate segment 431 along the axis to be disposed forwardly of the tip portion 413 of the catheter hub 41 so as to surround and sheathe the front segment 51 of the needle cannula 5 while permitting the tip end 52 to project forwardly of the distal segment 432 when the needle cannula 5 is placed in the position of use.

In use, after the tip protector 45 is removed, the tip end 52 of the needle cannula 5 is inserted into the patient's vein so as to introduce the tubular catheter 43 into the vein. Blood flowing into the flashback chamber 36 is visible from the intermediate portion 38 of the needle hub 3 so that the user can check whether the needle cannula 5 has been inserted properly into the vein. Referring to FIG. 5, the user can then separate the catheter hub 41 from the barrel 2 by holding the catheter hub 41 with one hand and holding and pulling the surrounding barrel wall 22 with the other hand. At the same time, the actuator 34 is operated with a finger of the hand holding the surrounding barrel wall 22 to move the engaging peg 33 rearwardly along the elongated guideway 23 so as to bring the needle hub 3 to the rear position, thereby placing the needle cannula 5 in the disposal position, where the front segment 51 retreats inwardly and rearwardly of the front open end 224 for safe disposal.

As illustrated, during operation, the user can hold the barrel 2 with one hand and operate the actuator 34 with a finger of the hand to cause the needle hub 3 to move to the rear position for drawing the used needle cannula 5 into the passage 21. Therefore, the operation is controllable by the user and is convenient to conduct. Besides, undesirable accidents can be avoided.

Figure 6:
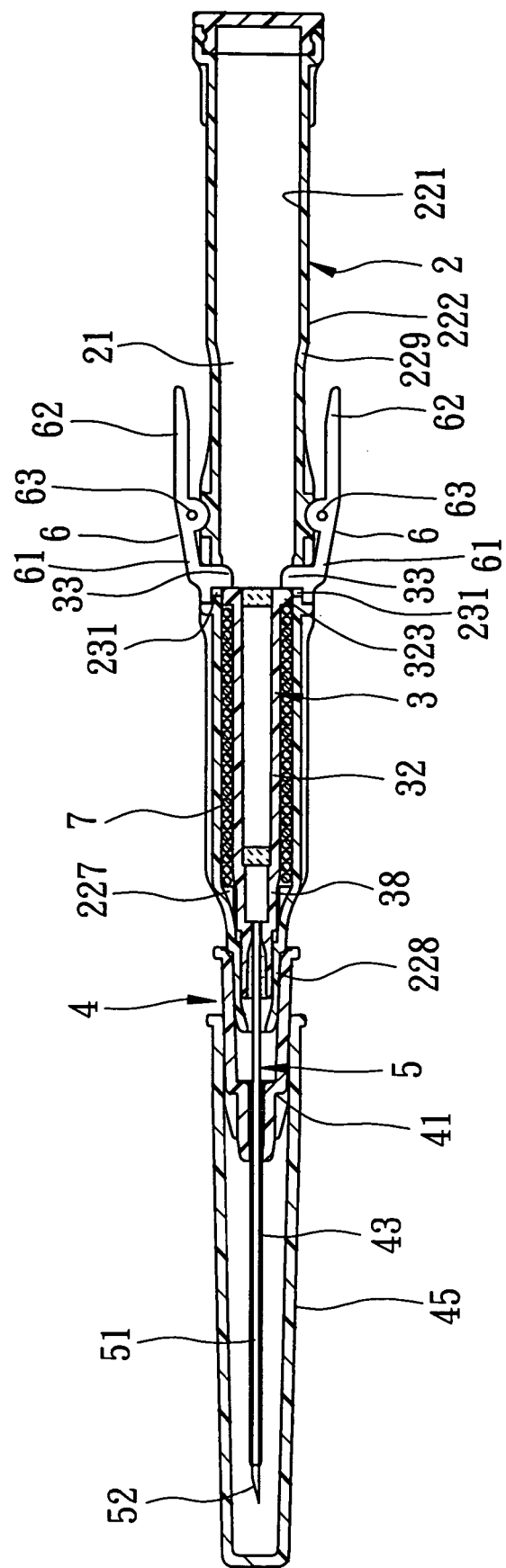
FIG. 6 is a sectional view of a second preferred embodiment of an intravenous catheter introducing device according to this invention in a ready-to-use position.
Figure 7:
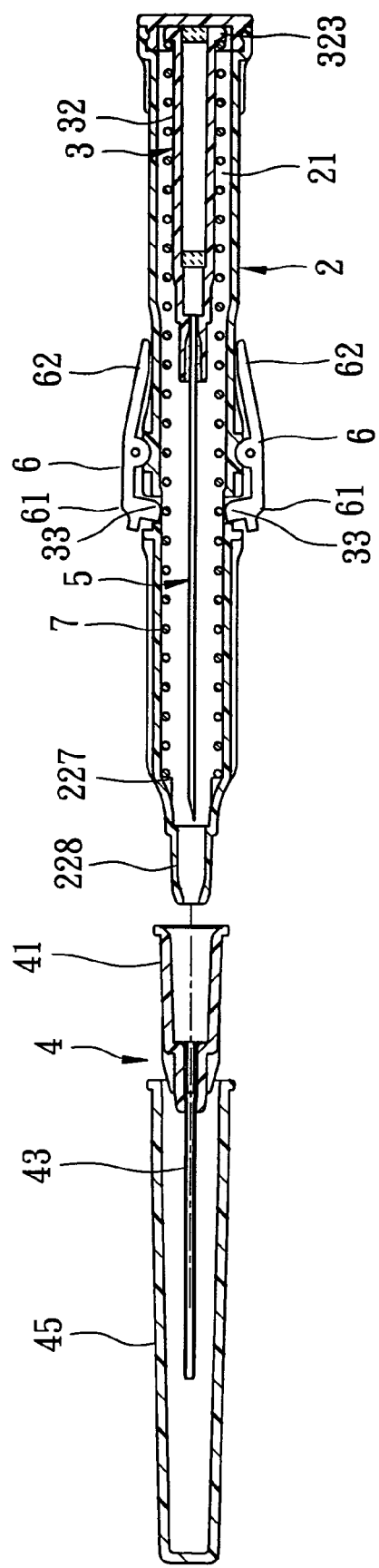
FIG. 7 is a sectional view of the second preferred embodiment in a retracted position.

Referring to FIGS. 6 and 7, the second preferred embodiment of an intravenous catheter introducing device according to this invention is shown to be similar to the first preferred embodiment in construction. The differences reside in that the releasably retaining member includes two retaining holes 231 formed in the larger-diameter wall portion 229, and that the actuator includes two triggering members 6 formed as levers. Each of the triggering members 6 is mounted pivotally on the outer barrel wall surface 222 at a fulcrum point 63, and includes a weight end 61 formed integrally with the engaging peg 33, and a power end 62 disposed at an opposite side of the weight end 61 relative to the fulcrum point 63 so as to be actuated to move the engaging peg 33 in the radial direction to withdraw the engaging peg 33 from the passage 21 in the barrel 2 to thereby release the needle hub 3.

Furthermore, the inner barrel wall surface 221 of the larger-diameter wall portion 229 has a shoulder 227 with ribs formed adjacent to the smaller-diameter wall portion 228. The rear shell portion 32 of the needle hub 3 has an annular rear flange 323 confronting the shoulder 227 in the longitudinal direction so as to define a biasing member receiving space therebetween and outside of the rear shell portion 32. A biasing member, such as a coiled spring 7, is received in the biasing member receiving space, and includes front and rear spring ends abutting against the ribs of the shoulder 227 and the flange 323, respectively, such that the coiled spring 7 is compressed by the needle hub 3 when the needle hub 3 is in the front position. Due to the provision of the coiled spring 7, when the power ends 62 of the triggering members 6 are depressed at the same time with the fingers to smoothly retract the engaging pegs 33 radially, the needle hub 3 is moved to the rear position so as to bring the needle cannula 5 to the disposal position, thereby preventing shaking of the needle cannula 5 during the retraction of the needle cannula 5 to help lessen the patient's pain.

It is noted that although the actuator in this embodiment is exemplified as including two triggering members 6, one triggering member 6 will be sufficient to perform the function of retaining and releasing the needle hub 3.

Figure 8:
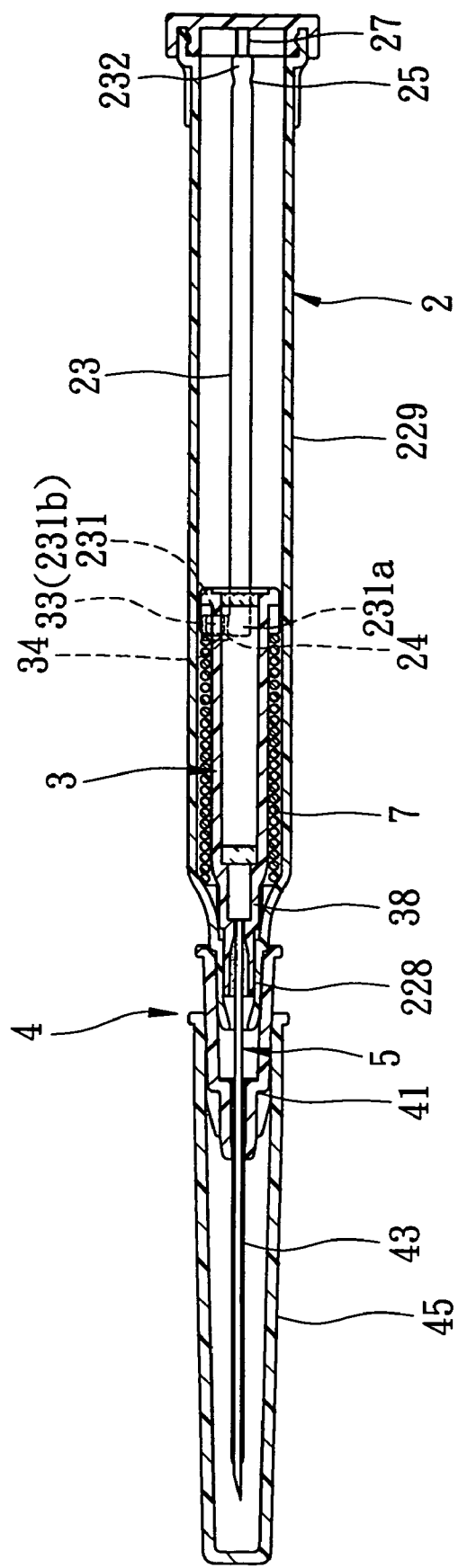
FIG. 8 is a sectional view of a third preferred embodiment of an intravenous catheter introducing device according to this invention in a ready-to-use position.
Figure 9:
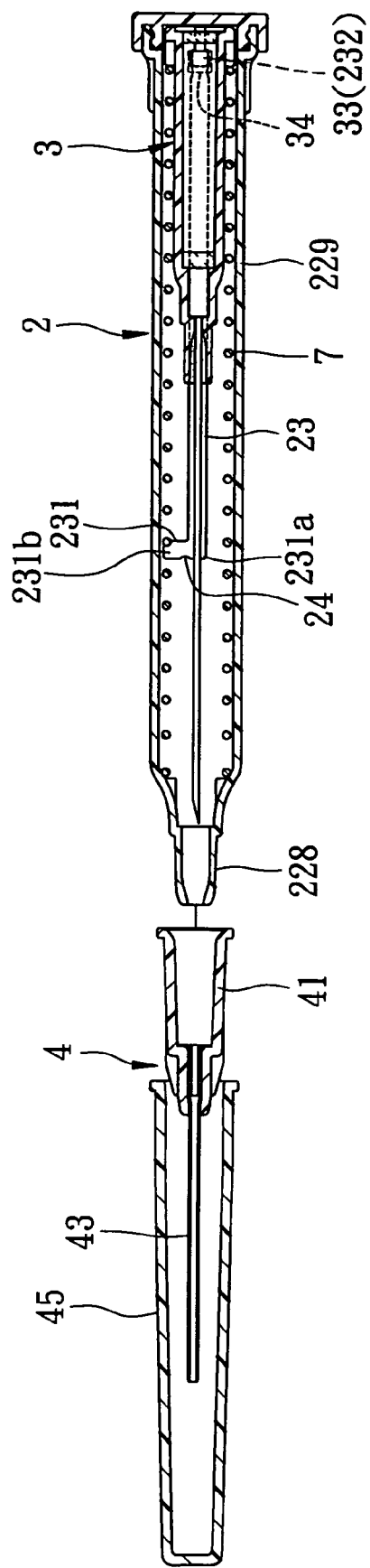
FIG. 9 is a sectional view of the third preferred embodiment in a retracted position.

Referring to FIGS. 8 and 9, the third preferred embodiment of an intravenous catheter introducing device according to this invention is shown to be similar to the first preferred embodiment in construction. In this embodiment, the retaining hole 231 includes a proximate connecting end 231a and a distal retaining end 231b which are opposite to each other in a transverse direction relative to the longitudinal direction, and which are proximate to and distal from the elongated guideway 23, respectively. The front constricted region 24 is formed between the proximate and distal connecting ends 231a,231b. As such, the engaging peg 33 is engaged in the distal retaining end 231b to arrest the needle hub 3 at the front position. Upon retraction of the needle cannula 5, the actuator 34 is operated to move the engaging peg 33 from the distal retaining end 231b to the proximate connecting end 231a so as to permit rearward movement of the needle hub 3 along the elongated guideway 23. A coiled spring 7 is also provided to bias the needle hub 3 to the rear position as in the second preferred embodiment.

Figure 10:
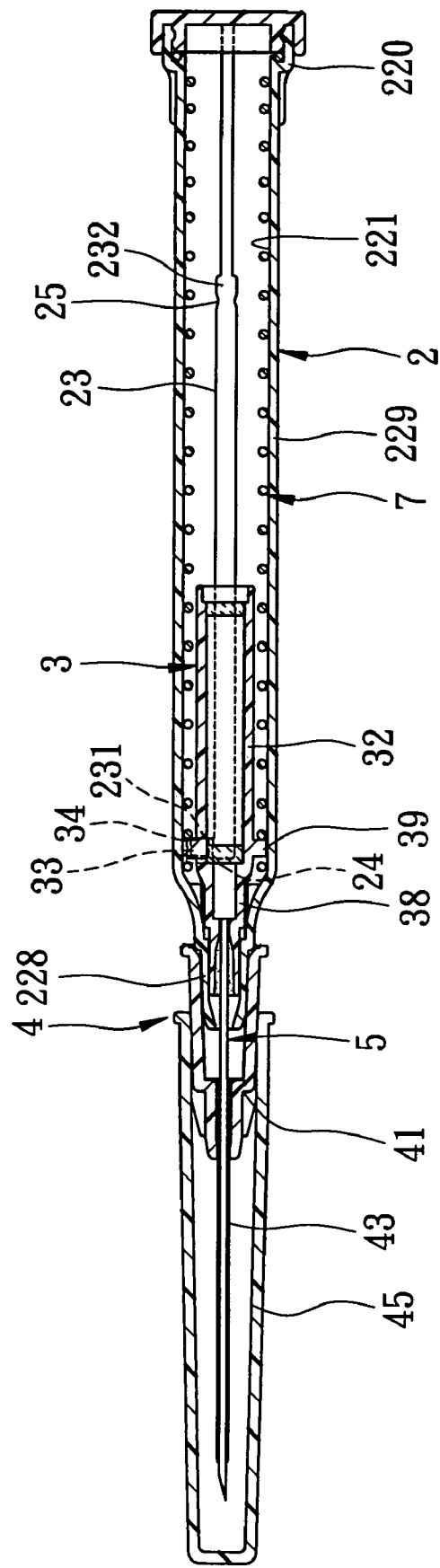
FIG. 10 is a sectional view of a fourth preferred embodiment of an intravenous catheter introducing device according to this invention in a ready-to-use position.
Figure 11:
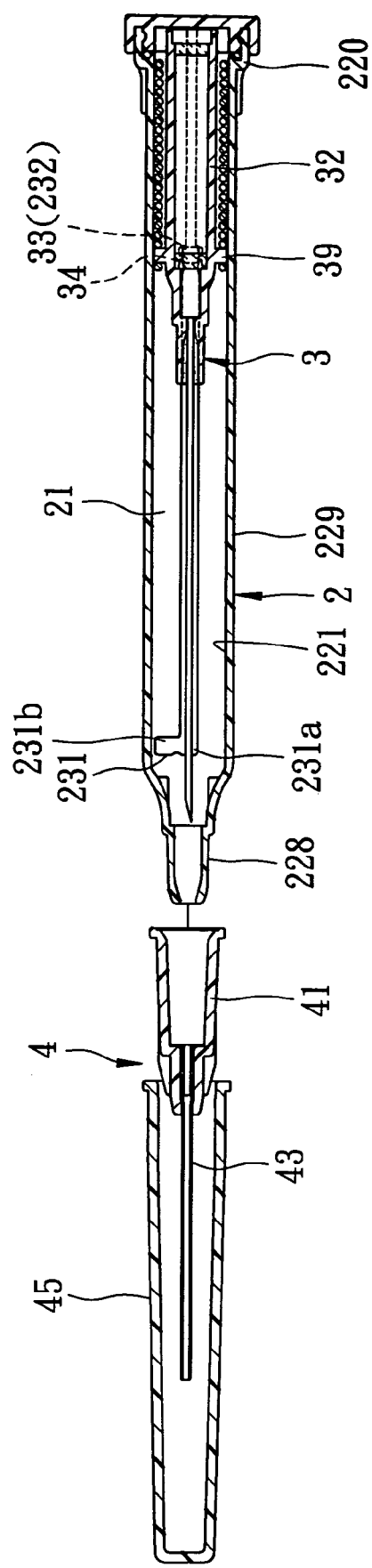
FIG. 11 is a sectional view of the fourth preferred embodiment in a retracted position.

Referring to FIGS. 10 and 11, the fourth preferred embodiment of an intravenous catheter introducing device according to this invention is shown to be similar to the third preferred embodiment in construction. The difference resides in that the rear shell portion 32 of the needle hub 3 and the inner barrel wall surface 221 of the larger-diameter wall portion 229 respectively have an annular flange 39 and an annular rear edge 220, which are opposite to and which confront each other in the longitudinal direction so as to define a biasing member receiving space therebetween and outside of the rear shell portion 32. The coiled spring 7 is received in the biasing member receiving space, and has front and rear spring ends secured to the flange 39 and the edge 220, respectively, such that the coiled spring 7 is tensioned by the needle hub 3 when the needle hub 3 is in the front position, as shown in FIG. 10. As illustrated in the third preferred embodiment, referring to FIG. 11, by operating the actuator 34 to move the engaging peg 33 from the distal retaining end 231b to the proximate connecting end 231a of the retaining hole 231, rearward movement of the needle hub 3 along the guideway 23 is permitted to enable the needle cannula 5 to be retracted into the passage 21.

Figure 12:
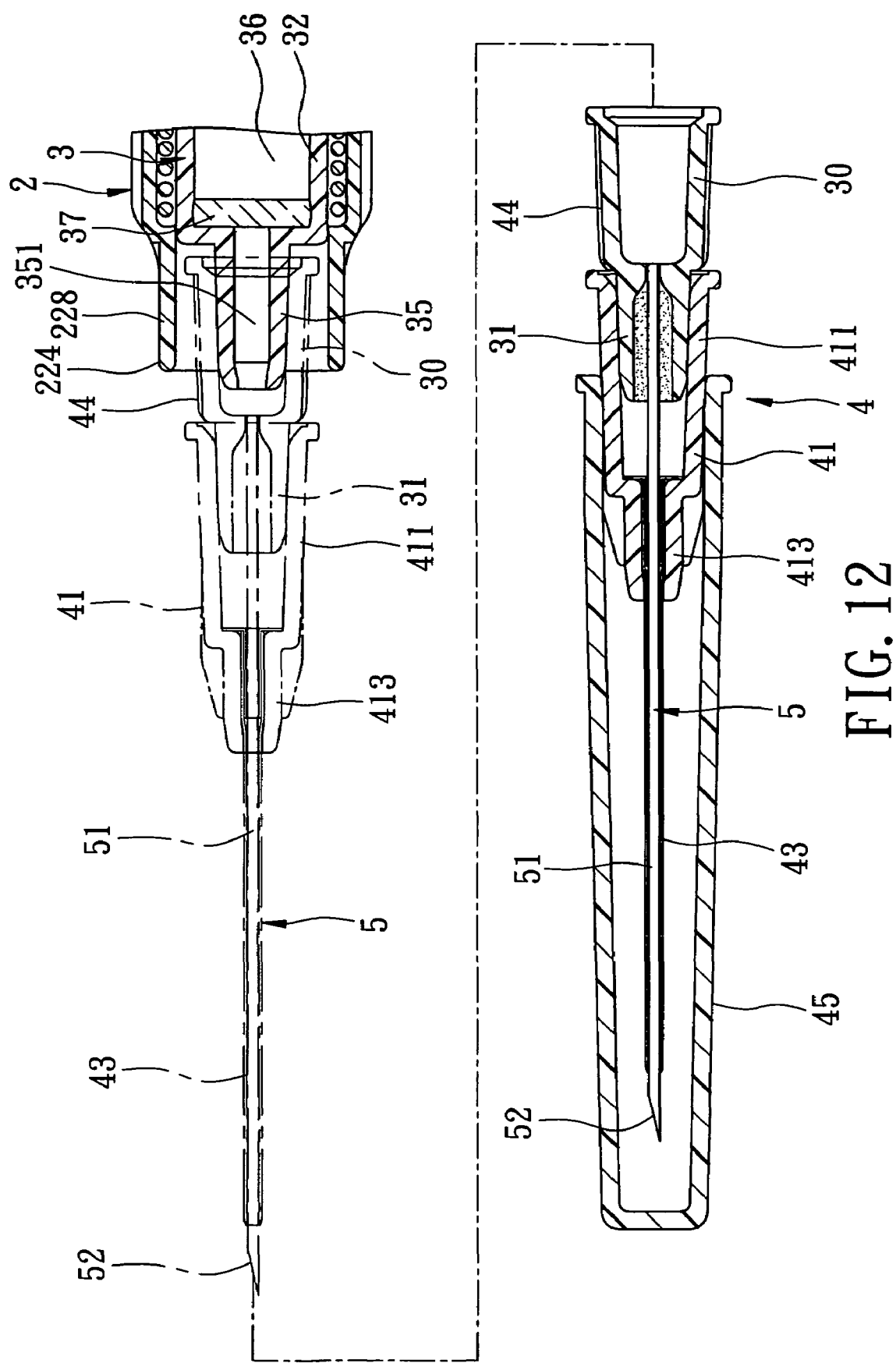
FIG. 12 is a fragmentary exploded sectional view of a fifth preferred embodiment of an intravenous catheter introducing device according to this invention.

Referring to FIG. 12, the fifth preferred embodiment of an intravenous catheter introducing device according to this invention is shown to be similar to the previous embodiments in construction. The differences reside in that the smaller-diameter wall portion 228 of the barrel 2 is formed to have an increased inner diameter of the front open end 224, and that the front holding portion 31 and the rear shell portion 32 of the needle hub 3 are separated from each other. In particular, the needle hub 3 further includes an interconnecting portion 35 which is formed integrally with and which extends forwardly from the rear shell portion 32 along the axis and which defines an axial passageway 351 that extends therethrough and that is communicated with the flashback chamber 36, and a sleeve portion 30 which is integrally formed with and which extends rearwardly from the front holding portion 31 along the axis so as to form a sleeve assembly 44. The sleeve portion 30 is detachably sleeved on the interconnecting portion 35 from the front open end 224 of the barrel 2 along the axis so as to fluidly communicate the needle cannula 5 with the flashback chamber 36. Thus, the combination of the catheter connection assembly 4 and the sleeve assembly 44, which is secured with the needle cannula 5 as a functional unit, can be used as a detachable unit with different catheter dimensions for various clinical applications.

Figure 13:
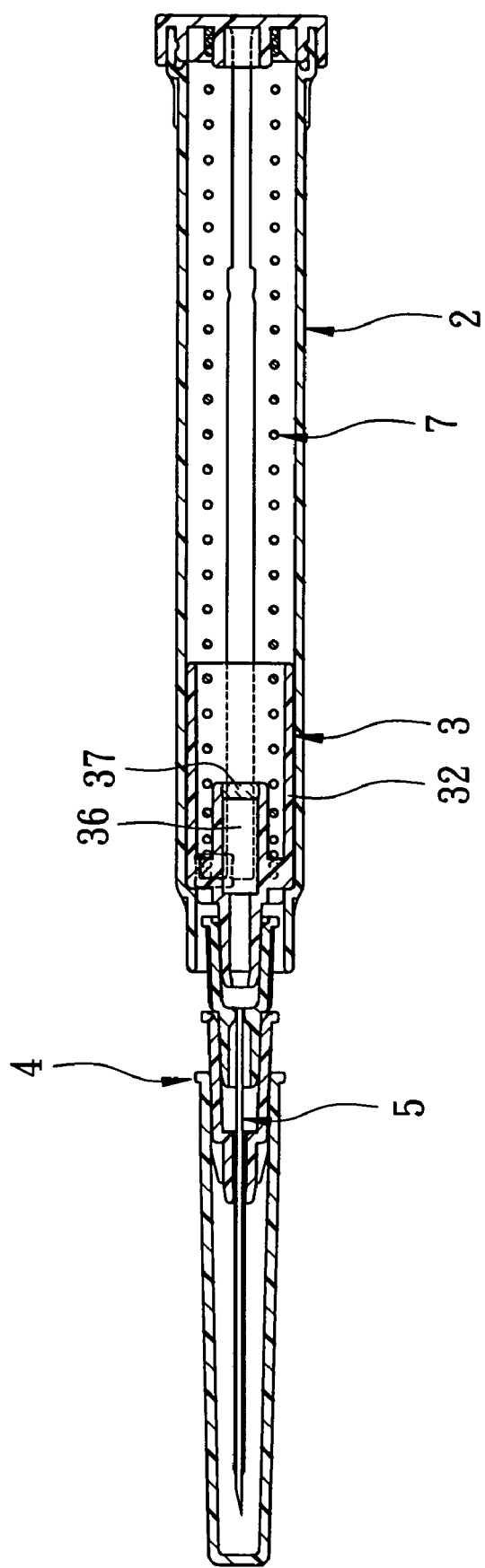
FIG. 13 is a sectional view of a sixth preferred embodiment of an intravenous catheter introducing device according to this invention in a ready-to-use position.

Referring to FIG. 13, the sixth preferred embodiment of an intravenous catheter introducing device according to this invention is shown to be similar to the fourth and fifth preferred embodiments in construction. The difference resides in that the coiled spring 7 has a smaller diameter, and has a front spring end received in the rear shell portion 32 of the needle hub 3 and which is secured to an inner edge of the rear shell portion 32, and a rear spring end which is secured to a closure cap 26.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

We claim:

1. An intravenous catheter introducing device comprising:
   a barrel having front and rear open ends opposite to each other in a longitudinal direction, and a surrounding barrel wall which interconnects and which is interposed between said front and rear open ends, said surrounding barrel wall including a front smaller-diameter wall portion and a rear larger-diameter wall portion which are opposite to each other in the longitudinal direction and which are proximate to said front and rear open ends, respectively, said surrounding barrel wall having an inner barrel wall surface which surrounds an axis in the longitudinal direction and which confines a passage that is communicated with said front and rear open ends, and an outer barrel wall surface opposite to said inner barrel wall surface in radial directions relative to the axis;
   a needle cannula having a front segment terminating at a tip end, and a rear connecting end opposite to said front segment along the axis;
   a needle hub including a front holding portion and a rear shell portion disposed opposite to each other along the axis, said front holding portion being received in said passage so as to be surrounded by said smaller-diameter wall portion, said rear shell portion being inserted into said passage from said rear open end, and being slidable relative to said surrounding barrel wall along the axis between front and rear positions to be proximate to said front open end and said rear open end, respectively, said front holding portion holding said rear connecting end of said needle cannula such that when said rear shell portion is in the front position, said needle cannula is placed in a position of use, where said front segment extends forwardly of said front open end for ready use, and when said rear shell portion is in the rear position, said needle cannula is placed in a disposal position, where said front segment retreats into said passage, said rear shell portion surrounding the axis and defining a flashback chamber which is fluidly communicated with said needle cannula;
   a releasably retaining member which is disposed to arrest axial movement of said needle hub relative to said barrel when said rear shell portion is in the front position, and which includes
      a retaining hole formed in said outer barrel wall surface of said larger-diameter wall portion, and extending in a radial direction through said inner barrel wall surface, and
      an engaging peg disposed to extend in the radial direction, and engageable in said retaining hole to establish an interengagement between said larger-diameter wall portion and said rear shell portion such that movement of said rear shell portion at the front position is arrested;
   an actuator operable externally and disposed to enable said engaging peg to be disengaged from said retaining hole so as to permit the axial movement of said needle hub to the rear position;
   a catheter hub including a sleeve portion which is detachably sleeved on said smaller-diameter wall portion and which defines a duct along the axis, and a tip portion which is opposite to said sleeve portion along the axis, and which defines a through hole that is communicated with said duct along the axis and that permits extension of said front segment therethrough; and
   a tubular catheter having a proximate segment which is inserted into said through hole and which extends along the axis to be fluidly communicated with said duct, and a distal segment which extends from said proximate segment along the axis to extend forwardly of said tip portion so as to surround and sheathe said front segment of said needle cannula while permitting said tip end to project forwardly of said distal segment when said needle cannula is placed in the position of use.

2. The intravenous catheter introducing device of claim 1, wherein said needle hub further includes an intermediate portion which interconnects said front holding portion and said rear shell portion to communicate said needle cannula with said flashback chamber and which is light transmissible to permit viewing of blood flowing therethrough.

3. The intravenous catheter introducing device of claim 2, wherein said needle hub further includes an air-permeable member which is in engagement with said rear shell portion so as to close said flashback chamber.

4. The intravenous catheter introducing device of claim 3, wherein said air-permeable member is made from a porous filter material.

5. The intravenous catheter introducing device of claim 1, wherein said rear larger-diameter wall portion has an elongated guideway extending from said outer barrel wall surface through said inner barrel wall surface in the radial direction, and elongated from said retaining hole rearwardly and in the longitudinal direction to terminate at a rear retaining end,
   said engaging peg being disposed on and extending radially from said rear shell portion to terminate at a shifted end which extends radially and outwardly of said outer barrel wall surface, and being slidable along said elongated guideway from said retaining hole to said rear retaining end when said rear shell portion of said needle hub slides from the front position to the rear position,
   said actuator being connected to said shifted end of said engaging peg, and being disposed outwardly of and being slidable relative to said outer barrel wall surface.

6. The intravenous catheter introducing device of claim 5, wherein said elongated guideway has front and rear constricted regions which are formed immediately behind said retaining hole and immediately in front of said rear retaining end, respectively, such that once said engaging peg is forced through one of said front and rear constricted regions, movement of said engaging peg is arrested by virtue of a snap-fit in a corresponding one of said retaining hole and said rear retaining end so as to place said needle hub in a corresponding one of the front and rear positions.

7. The intravenous catheter introducing device of claim 6, wherein said rear larger-diameter wall portion further has a split which extends from said rear retaining end of said elongated guideway to said rear open end.

8. The intravenous catheter introducing device of claim 5, wherein said retaining hole includes a proximate connecting end and a distal retaining end which are opposite to each other in a transverse direction relative to the longitudinal direction and which are proximate to and distal from said elongated guideway, respectively, such that said engaging peg is engaged in said distal retaining end to arrest movement of said rear shell portion of said needle hub at the front position, and such that said actuator is operated to move said engaging peg from said distal retaining end to said proximate connecting end so as to permit slidable movement of said engaging peg along said elongated guideway.

9. An intravenous catheter introducing device comprising:
a barrel having front and rear open ends opposite to each other in a longitudinal direction, and a surrounding barrel wall which interconnects and which is interposed between said front and rear open ends, said surrounding barrel wall including a front smaller-diameter wall portion and a rear larger-diameter wall portion which are opposite to each other in the longitudinal direction and which are proximate to said front and rear open ends, respectively, said surrounding barrel wall having an inner barrel wall surface which surrounds an axis in the longitudinal direction and which confines a passage that is communicated with said front and rear open ends, and an outer barrel wall surface opposite to said inner barrel wall surface in radial directions relative to the axis;
a needle cannula having a front segment terminating at a tip end, and a rear connecting end opposite to said front segment along the axis;
a needle hub including a front holding portion and a rear shell portion disposed opposite to each other along the axis, said rear shell portion being inserted into said passage from said rear open end, and being slidable relative to said surrounding barrel wall along the axis between front and rear positions to be proximate to said front open end and said rear open end, respectively, said front holding portion holding said rear connecting end of said needle cannula such that when said rear shell portion is in the front position, said needle cannula is placed in a position of use, where said front segment extends forwardly of said front open end for ready use, and when said rear shell portion is in the rear position, said needle cannula is placed in a disposal position, where said front segment retreats into said passage, said rear shell portion surrounding the axis and defining a flashback chamber which is fluidly communicated with said needle cannula;
a releasably retaining member which is disposed to arrest axial movement of said needle hub relative to said barrel when said rear shell portion is in the front position, and which includes
a retaining hole formed in said outer barrel wall surface of said larger-diameter wall portion, and extending in a radial direction through said inner barrel wall surface, and
an engaging peg disposed to extend in the radial direction, and engageable in said retaining hole to establish an interengagement between said larger-diameter wall portion and said rear shell portion such that movement of said rear shell portion at the front position is arrested;
an actuator operable externally and disposed to enable said engaging peg to be disengaged from said retaining hole so as to permit the axial movement of said needle hub to the rear position, said actuator including a triggering member which is pivotally mounted on said outer barrel wall surface at a fulcrum point, and which includes a weight end that is formed integrally with said engaging peg, and that is disposed rearwardly of said rear shell portion so as to bring said engaging peg to abut against said rear shell portion when said needle cannula is in the position of use, and a power end disposed at an opposite side of said weight end relative to said fulcrum point so as to be actuated to move said engaging peg in the radial direction to withdraw said engaging peg from said passage,
a biasing member which is disposed between said rear shell portion and said inner barrel wall surface to bias said needle hub toward the rear position;
a catheter hub including a sleeve portion which is detachably sleeved relative to said front holding portion of said needle hub and which defines a duct along the axis, and a tip portion which is opposite to said sleeve portion along the axis, and which defines a through hole that is communicated with said duct along the axis and that permits extension of said front segment therethrough; and
a tubular catheter having a proximate segment which is inserted into said through hole and which extends along the axis to be fluidly communicated with said duct, and a distal segment which extends from said proximate segment along the axis to extend forwardly of said tip portion so as to surround and sheathe said front segment of said needle cannula while permitting said tip end to project forwardly of said distal segment when said needle cannula is placed in the position of use.

10. An intravenous catheter introducing device comprising:
a barrel having front and rear open ends opposite to each other in a longitudinal direction, and a surrounding barrel wall which interconnects and which is interposed between said front and rear open ends, said surrounding barrel wall including a front smaller-diameter wall portion and a rear larger-diameter wall portion which are opposite to each other in the longitudinal direction and which are proximate to said front and rear open ends, respectively, said surrounding barrel wall having an inner barrel wall surface which surrounds an axis in the longitudinal direction and which confines a passage that is communicated with said front and rear open ends, and an outer barrel wall surface opposite to said inner barrel wall surface in radial directions relative to the axis;
a needle cannula having a front segment terminating at a tip end, and a rear connecting end opposite to said front segment along the axis;

a needle hub including a front holding portion and a rear shell portion disposed opposite to and separated from each other along the axis, said rear shell portion being inserted into said passage from said rear open end, and being slidable relative to said surrounding barrel wall along the axis between front and rear positions to be proximate to said front open end and said rear open end, respectively, said front holding portion holding said rear connecting end of said needle cannula such that when said rear shell portion is in the front position, said needle cannula is placed in a position of use, where said front segment extends forwardly of said front open end for ready use, and when said rear shell portion is in the rear position, said needle cannula is placed in a disposal position, where said front segment retreats into said passage, said rear shell portion surrounding the axis and defining a flashback chamber which is fluidly communicated with said needle cannula, said needle hub further including an interconnecting portion which is formed integrally with and which extends forwardly from said rear shell portion along the axis and which defines an axial passageway that extends therethrough and that is communicated with said flashback chamber, and a sleeve portion which is integrally formed with and which extends rearwardly from said front holding portion along the axis and which is detachably sleeved on said interconnecting portion from said front open end of said barrel along the axis so as to fluidly communicate said needle cannula with said flashback chamber;

a releasably retaining member which is disposed to arrest axial movement of said needle hub relative to said barrel when said rear shell portion is in the front position, and which includes a retaining hole formed in said outer barrel wall surface of said larger-diameter wall portion, and extending in a radial direction through said inner barrel wall surface, and an engaging peg disposed to extend in the radial direction, and engageable in said retaining hole to establish an interengagement between said larger-diameter wall portion and said rear shell portion such that movement of said rear shell portion at the front position is arrested;

an actuator operable externally and disposed to enable said engaging peg to be disengaged from said retaining hole so as to permit the axial movement of said needle hub to the rear position;

a catheter hub including a sleeve portion which is detachably sleeved on said front holding portion of said needle hub and which defines a duct along the axis, and a tip portion which is opposite to said sleeve portion along the axis, and which defines a through hole that is communicated with said duct along the axis and that permits extension of said front segment therethrough; and a tubular catheter having a proximate segment which is inserted into said through hole and which extends along the axis to be fluidly communicated with said duct, and a distal segment which extends from said proximate segment along the axis to extend forwardly of said tip portion so as to surround and sheathe said front segment of said needle cannula while permitting said tip end to project forwardly of said distal segment when said needle cannula is placed in the position of use.

11. The intravenous catheter introducing device of claim 10, further comprising a biasing member which is interposed between said rear shell portion and said inner barrel wall surface, and which is disposed to bias said needle hub toward the rear position.

* * * * *